United States Patent
Probasco et al.

(10) Patent No.: US 8,153,146 B2
(45) Date of Patent: Apr. 10, 2012

(54) PESTICIDE AND FUNGICIDE TREATMENTS MADE FROM HOP EXTRACTS

(75) Inventors: Gene Probasco, Yakima, WA (US);
Mark M. Bossert, Yakima, WA (US);
David W. Hysert, Yakima, WA (US)

(73) Assignee: John I. Haas, Washington, DC (US)

( * ) Notice: Subject to any disclaimer, the term of this patent is extended or adjusted under 35 U.S.C. 154(b) by 377 days.

(21) Appl. No.: 10/805,876

(22) Filed: Mar. 22, 2004

(65) Prior Publication Data

US 2005/0043404 A1 Feb. 24, 2005

Related U.S. Application Data

(63) Continuation-in-part of application No. 10/212,982, filed on Aug. 5, 2002, now abandoned, and a continuation of application No. 09/573,332, filed on May 17, 2000, now abandoned.

(51) Int. Cl.
*A01N 25/32* (2006.01)
*A01N 25/02* (2006.01)

(52) U.S. Cl. ........ 424/406; 424/405; 424/725; 424/773; 424/774; 424/776; 424/778; 424/779; 514/690

(58) Field of Classification Search .................. None
See application file for complete search history.

(56) References Cited

U.S. PATENT DOCUMENTS

| | | | |
|---|---|---|---|
| 3,615,660 A | 10/1971 | Bavisotto et al. | |
| 3,886,171 A * | 5/1975 | Parsons | 546/309 |
| 4,148,873 A | 4/1979 | Owades | |
| 4,170,638 A | 10/1979 | Owades | |
| 5,227,162 A | 7/1993 | Ferrari et al. | |
| 5,372,817 A * | 12/1994 | Locke et al. | 424/405 |
| 5,827,895 A * | 10/1998 | Nutter et al. | 514/690 |
| 6,096,350 A | 8/2000 | Kemp et al. | |
| 6,204,283 B1 | 3/2001 | Black et al. | |
| 2001/0014346 A1 | 8/2001 | Watkins | |
| 2002/0051804 A1 | 5/2002 | Probasco et al. | |
| 2003/0060379 A1 * | 3/2003 | Souter et al. | 510/131 |
| 2005/0049230 A1 | 3/2005 | Henrich et al. | |
| 2005/0220914 A1 | 10/2005 | Probasco et al. | |
| 2006/0009122 A1 | 1/2006 | Swanson | |
| 2006/0013870 A1 | 1/2006 | Kuhrts | |

FOREIGN PATENT DOCUMENTS

GB 2330076 * 4/1999

OTHER PUBLICATIONS

Losel et al The potential of fsemiiochemicals for control of Phordon humuli—Pestic. Sci. 48, 293-303, 1996.*
Jones eta l Repellent and Oviposition-deterring effects of Hop Beta-acids on the two-spotted spider Mite—Pestic. ci. 47 pp. 165-169, 1996.*
Jones, G., "Potential Control of Two-Spotted Spider Mite, Tetranychus Urticae Koch, Using Hop β-Fraction," (1998) pp. 1-165, A thesis submitted for the degree of Doctor of Philosophy of the Univeristy of London and for the Diploma of Imperial College of Science, Technology & Medicine.
"Culpeper's Complete Herbal a book of Natural Remedies for Ancient Ills," Wordsworth Reference, pp. 134-135 (1995).
International Search Report for PCT/US07/23984.

* cited by examiner

*Primary Examiner* — Neil Levy
(74) *Attorney, Agent, or Firm* — Edwards Wildman Palmer LLP; Jeffrey D. Hsi; Melissa Hunter-Ensor, Esq.

(57) ABSTRACT

The invention is an organic pesticide or fungicide made from components of hop extract by preparing stable aqueous emulsions of hop acids and other hop extract components. The hop acids and other hop extract components are suspended as stable, colloidal preparations in water, which can be sprayed on plants for pest control.

11 Claims, No Drawings

PESTICIDE AND FUNGICIDE TREATMENTS MADE FROM HOP EXTRACTS

RELATED APPLICATIONS

This specification is a continuation-in-part of application Ser. No. 10/212,982, filed Aug. 5, 2002, now abandoned. Application Ser. No. 10/212,982 was a continuation of application Ser. No. 09/573,332, filed May 17, 2000, now abandoned.

TECHNICAL FIELD

The invention disclosed here generally relates to pesticides and fungicides. More particularly, it relates to the use of components of hop extracts as a pesticide, fungicide, or for the treatment of other plant diseases.

BACKGROUND OF THE INVENTION

Chemical pesticides are used in commercial agriculture, home gardening, residential use, and similar applications for the purpose of controlling insects and spiders. There are well-known environmental and health concerns associated with using chemical pesticides, herbicides, or fungicides. For example, in some instances, it has been proven that the long-term use of certain chemical pesticides creates environmental problems. A well-known example involved the ban of DDT in the United States.

Ongoing health concerns about chemical pesticides have given rise to an emerging market for "organic" pesticides. Insecticidal soap is a typical example of an organic pesticide in use today.

Organic pesticides are generally deemed to be less effective than chemical pesticides. There is a trade-off when comparing one to the other. Chemical pesticides have a higher level of toxicity and provide better pest control. However, higher toxicity also heightens environmental concerns. The same level of environmental concern does not attach to organic pesticides, but at the price of effective pest control.

Hope cones contain lupulin glands that have two important bittering substances: alpha acids and beta acids. These acids are sometimes called humulones and lupulones, respectively. Hop acids were initially used as a preservative agent for beer prior to the existence of refrigeration. Today, they are primarily used to create the bitter taste and flavor of beer.

The term "hop acids," as used here, means alpha acids, beta acids, mixtures of these acids, and/or other components found in hop extracts; for example, beta fraction, essential oils, waxes, and uncharacterized resins. The term "hop acids" also includes all forms of modified hop acids; for example, iso-alpha acids, tetra-hydro-iso-alpha acids, rho-iso-alpha acids, hexa-hydro-iso-alpha acids, and hexa-hydro-beta acids. As is well known, alpha acids consist of mixtures of analogues, primarily humulone, cohumulone, adhumulone, and other minor constituents. Similarly, beta acids consist of mixtures of analogues, primarily lupulone, colupulone, adlupulone, and other minor constituents. For these reasons, alpha and beta acids are referred to in the plural.

A number of companies are in the business of producing hop extracts for the brewing industry. These extracts come from the hops that are grown in various regions of the world. In some respects, the hop extract industry is a combination of agriculture and chemistry. On the agricultural side, hop growers have many of the same kinds of problems with pests as the growers of other food products. For example, spider mites, which are a common agricultural pest, are also a problem for hop growers.

Agricultural crops are also affected by powdery mildew, mold, and other kinds of blight or disease. Powdery mildew is particularly a problem for hop growers.

Given that people have been drinking hop acids as part of beer for many centuries, hop acids are a proven organic consumable. Hops are one of the basic ingredients of beer and, as such, hops and hop extracts are considered GRAS (Generally Recognized As Safe) by the U.S. Food and Drug Administration ("FDA").

Those who work with hop extracts have discovered that the beta fraction of hop acids dissolved in ethanol or xylene can be toxic to spider mites. Hop acids and other components of hop extracts are not highly soluble in water, but are quite soluble in non-aqueous solvents like ethanol or xylene. However, such non-aqueous solvents are undesirable carriers for the application of pesticides to plants. Therefore, while water is an essential carrier for pesticide application to plants, because of solubility problems, water is not easy to use as a carrier if hop acids are the active agent.

The present invention provides a way to use water as the carrier for delivering hop acids as a pesticide, fungicide, or the like.

SUMMARY OF THE INVENTION

The invention is a treatment solution made from hop acids and related hop extract components that can be used as a pesticide, fungicide, or blight or disease treatment of plants. The treatment solution can be made by creating an aqueous emulsion of hop acids. An "emulsion" is different from a solution and enables hop acids and other hop extract components to be applied to plants as part of a water-based spray, rather than using a non-aqueous solvent.

Hop acids are not highly soluble in water. However, stable aqueous solutions of certain hop acids can be prepared by the selection of appropriate concentration and pH. Further, it is possible to prepare these aqueous emulsions as colloidal suspensions in water (i.e., emulsions) that will not separate over time. Moreover, these emulsions can be diluted with water as required by the end user for spraying.

Although the emulsions are stable, they are also susceptible to film creation. Films are problematical with spray applicators in the field. Regardless of the effectiveness of the treatment solution with respect to controlling either pests or plant diseases, the solution cannot be applied effectively if it causes spray nozzles to clog on a continuous basis.

We have been engaged in the ongoing development of formulations of hop acids for use as treatment solutions for pests and plant diseases. Our initial formulations involved experimenting with 10% solutions of hop acids diluted with water and an emulsifier to create a stable aqueous emulsion. These initial studies involved the preparation of emulsions from beta fraction (beta acid oil), beta acids, and alpha acids. Subsequent studies involved the use of beta acids with the concentration reduced from 10% to 1%. Moreover, it was discovered that the film or residue problem described above can be improved considerably by adding liquid soap to the treatment solution at a low concentration.

BEST MODE FOR CARRYING OUT THE INVENTION

A. Initial Tests.

The following description sets forth examples for creating stable 10% solutions of hop acids or 10% emulsions of hop acids that can be diluted with water to the desired degree to produce stable aqueous emulsions that can then be used as spray-on treatment solutions. These treatment solutions may have use as pesticides, fungicides, or for the treatment of other kinds of plant diseases. The diluted emulsions remain stable at all dilutions. What this means is that concentrated solutions and/or emulsions can be sold as organic pesticides and later diluted by the user.

We initially developed three basic formulations. The first formulation was a 10% emulsion of beta fraction. This emulsion can be diluted with water to any degree to form further stable emulsions. The second and third formulations involved the preparation of 10% solutions of alpha and beta acids. These aqueous solutions convert to stable, aqueous emulsions upon the addition of water and likewise can be diluted to a lower concentration. Specific examples of these formulations are set forth below.

1. Preparation of 10% Emulsion of Beta Fraction (Beta Acid Oil) for Pest Control.

The term "beta fraction" refers to the oily, waxy, resinous portion of the hop extract obtained when the hop extract is washed with caustic water to remove most of the alpha acids. The beta fraction contains mostly beta acids, resins, oils, and waxes; it is also called beta acid oil.

To prepare an aqueous emulsion of beta fraction, the beta fraction was heated to 60 C, and added to a volume of 60 C water, to which an emulsifier, such as an alkanolamide (e.g., Ninol FM Tri-Emulsifier), was added. Ninol FM Tri-Emulsifier is available from Northwest Agricultural Products, 821 South Chestnut, Pasco, Wash. 99302 (509-547-8234). The mixture was then emulsified in a high-shear mixer to produce a stable emulsion. As an example, to produce .about 1 Kg of beta fraction emulsion, 100 g of beta fraction was heated to 60 C, and 890 grams of water was heated separately to 60 C. The warm beta fraction and water were mixed together, and 10 grams of Ninol emulsifier was added to the mixture (the addition of as little as 0.2% emulsifier will produce a stable emulsion; adding up to 2% emulsifier will increase beta fraction utilization). This mixture was placed in a high-shear mixer (a Warring kitchen blender on high speed), mixed for 60-90 seconds, poured into a container, and let sit for 2-3 minutes or until any foam collapsed. Any of the beta fraction that would not emulsify was separated. The aqueous emulsion was decanted, and any beta fraction or foam that did not go into the aqueous emulsion was discarded.

A 10% beta fraction aqueous emulsion prepared as described in the above example is a stable emulsion. When diluted with tap water or well water, it forms similarly stable aqueous emulsions at all dilutions.

2. Preparation of 10% Aqueous Beta-Acids Solution for Pest Control

Beta fraction was the starting material used to prepare a 10% aqueous beta-acids solution. The beta fraction may be used as is or washed with caustic water to reduce the alpha-acids concentration in the beta fraction so that the ratio of alpha-acids to beta-acids is 0.05, or below, by HPLC analysis. The temperature of the beta fraction was raised to 60° C. with continuous mixing, and caustic was added in the form of KOH to bring the pH to 10-11. Having first determined the beta-acids content in the beta fraction by HPLC analysis, a volume of 60° C. water was added, while mixing, so that the beta-acids concentration of the aqueous phase was between 10% and 50%. The pH of the solution was adjusted, if necessary, to 10-11 at 60° C. It was necessary to subtract the volume of KOH added for pH adjustment from the calculated volume of water. Also, a temperature range of 55-70° C. was acceptable, although 60° C. was optimal. Mixing was stopped, and the mixture was allowed to sit for at least 45 minutes, during which time the temperature of the solution was maintained at 60° C. The aqueous beta-acids phase was then separated from the resinous phase. The aqueous phase was diluted to a concentration of 10% beta acids by HPLC, while the temperature was maintained at 60° C., and the pH kept at 10-11. The aqueous phase was cooled (mixing is optional) to 1-13° C., and allowed to sit for at least 2 hours. The solution was then decanted or filtered.

Small-Scale 10% Beta Acids Example:

500 g of beta fraction containing 50% beta-acids by HPLC was heated to 60° C. Approximately 250 mL of 20% KOH was added while stirring, with heat to maintain a 60° C. temperature, and to bring the pH up to 10.7. Mixing was stopped, and the mixture was allowed to sit overnight. The following morning, the resinous fraction was set aside and the aqueous fraction was heated to 60° C. and analyzed by HPLC. Water and 20% KOH were added to bring the beta acids concentration to 10%, and the pH to 10.7. The aqueous beta acids solutions was refrigerated to 5° C. overnight, and filtered the next morning.

Large-Scale 10% Beta Acids Example:

1000 kg of beta fraction at 60° C. was placed in a hot water-jacketed tank. Approximately 120 gallons of 20% KOH was added with continuous mixing until the pH of the aqueous phase reached 10.7. The mixing was shut down, but the heat was maintained at 60° C., and the mixture was allowed to sit overnight. The aqueous layer was pumped into a stainless steel, heat-jacketed tank and diluted to a 10% beta-acids concentration by HPCL using deionized water. The temperature and pH were maintained at 60° C. and 10.7, respectively. Heating of the tank was stopped, the product was cooled to 10° C., and the allowed to settle overnight. Clouded and precipitated material was pumped to a recycle tank, and the clear beta-acids solution was filtered.

10% beta-acids solution is relatively easy to make (see above examples). It is a clear solution with no precipitated material. It is similar in color, clarity, and consistency to weak iced tea. However, the stability is not robust, however. A change in temperature can cause cloudiness to appear. Also, if it is diluted with cold (or even warm) water after it is formulated, it becomes cloudy immediately.

Dilution of 10% beta-acids solution with tap water or well water results in the formation of a stable aqueous emulsion. It has the appearance of milk and does not exhibit any separation even during days of storage. It was very stable, and no precipitate formed, even down to a dilution of 1:16. Also, as the solution was diluted with water, only a minor change in the pH occurred. It dropped by about 0.5 pH units, certainly not enough to be the cause of precipitation. No difference was observed when 0.4% Ninol emulsifier was added.

3. Preparation of 10% Aqueous Alpha-Acids Solution for Pest Control General Example:

Supercritical $CO_2$ Nugget extract was used to prepare 10% aqueous alpha-acids solution; however, one may start with hop extract of any type or variety. The hop extract was placed in a volume of water calculated to produce an aqueous alpha-acids solution, with a concentration of 3-20% by HPLC. An alpha acid concentration of less than 8% was optimum. At this concentration, beta acid solubility in the aqueous phase was lowered. The temperature was raised to 50-70° C., and the pH was adjusted to 6-8, with constant mixing. A pH of 7-8 was optimum. The extract solution was then allowed to sit for at least 45 minutes. The resinous fraction containing beta-acids, oils, and waxes was set aside, while the aqueous alpha-acids solution was decanted. The temperature was raised to 60° C. and the pH was raised to 7-9. The solution was analyzed by HPLC.

If the alpha-acids concentration was 10% or greater, water was added to bring the concentration to 10%. The solution was cooled to 1-19° C., and filtered or decanted.

If the alpha-acids concentration was less than 10%, the aqueous solution was acidified ($H_2SO_4$ or $H_3PO_4$ were satisfactory) at 60° C. to bring the alpha-acids out of solution. The alpha-acids were washed with fresh 60° C. water and allowed to sit for a minimum of 45 minutes. The water was discarded, and a calculated volume of 60° C. fresh water was added. The volume was calculated to produce a 10% alpha acid concentration by HPLC, also taking into account the volume of caustic necessary for pH adjustment. The alpha-acids solution was heated to 60° C., and the pH was raised to 7-9 with KOH solution. The aqueous solution was allowed to cool to 1-19° C., and filtered or decanted.

Small-Scale Example of 10% Aqueous Alpha-Acids Solution:

800 g of supercritical $CO_2$ Nugget extract was added to 2700 mL of deionized water, and the temperature was increased, with constant mixing, to 60° C. Approximately 300 mL of 20% KOH was added to bring the pH up to 7.7. The solution was allowed to sit overnight. The resinous fraction containing beta-acids, oils, and waxes was set aside, while the aqueous alpha-acids solution was decanted and cooled overnight to 7° C. The aqueous solution was then filtered, while cold, to remove any crystallized beta fraction, and brought back to 60° C. 20% $H_2SO_4$ was added with continuous stirring until the pH was 2.5. The resinous alpha-acids were separated and washed with fresh 60° C. deionized water. The alpha-acids were added to 2000 mL deionized water and brought to 60° C. Approximately 300 mL of 20% KOH was added to bring the pH up to 8.0, and the solution was analyzed by HPLC. Deionized water and 20% KOH were added to bring the concentration and pH up to 10% and 8.9, respectively. The solution was cooled to 5° C. overnight, and filtered.

10% alpha-acids solution is also relatively easy to make (see above example) and is a clear solution with no precipitated material. Like the beta acids formulation, it is similar in color, clarity, and consistency to weak iced tea. The stability is not robust and a change in temperature can cause cloudiness to appear.

Dilution of 10% alpha-acids solution with tap water or well water results in the formation of a stable aqueous emulsion which has the appearance of milk and does not exhibit any separation, even after days of storage. It was found to be very stable down to a dilution of 1:16, and no precipitate formed. Also, as the solution was diluted with water, only a minor change in the pH occurred. It dropped by about 0.5 pH units, certainly not enough to be the cause of the precipitation. No difference was observed when 0.4% Ninol emulsifier was added.

4. Method of Application

The above emulsions were sprayed on plants according to the following procedure:

The above-concentrated formulations were diluted with tap water to the desired concentration and the diluted portion agitated by shaking prior to spray application. Application of formulations to hop leaves in the laboratory was accomplished by a hand-held and manually-operated bottle sprayer of 500 mL volume, with finger lever action and nozzle adjusted to the finest droplet size.

Application of each formulation consisted of two pulls of the sprayer lever with the nozzle 12 inches from the leaf surface. Each double pull of the lever applied approximately 2 milliliters of liquid to an area of approximately one square foot. The spray pattern did not provide droplet density sufficient to cover 100% of the leaf area, but droplets were close enough to each other to cover about 50% of the leaf area. Treated hop leaves were placed inside plastic bags at approximately 22 degrees centigrade. Each treatment consisted of 4 hop leaves.

5. Initial Results

Tests were made on the two-spotted spider mite pest (*Tetranychus urticae*), on the beneficial predator mite (*Galendromus occidentalis*), and on the green peach aphid (*Myzus persicae*). Mortality was determined after 24 hours for pest mites, 48 hours for beneficial mites, and 72 hours for aphids.

A 1:16 dilution of the original 10% concentrations resulted in an applied concentration of 0.625% for each formulation described above. At this concentration and under the described conditions, all three formulations produced 100% mortality of the treated pest mites within 24 hours of application, while the mortality of the beneficial mites was much less at about 25% after 48 hours.

Concentrations of 10% produced the immediate death of about 30% of the aphids present for each formulation. Greater dilutions produced fewer immediate mortalities.

B. Field Tests.

We conducted a confidential field trial using a beta acid emulsion for the purpose of determining effectiveness with respect to the control of two-spotted spider mites on commercial hops. These field tests involved applying a 1% beta acid emulsion to three plots at the rate of 15, 200, and 100 gallons per acre, respectively. The 15 gallon plot was treated with a tower sprayer. The 100 and 200 gallon plots were treated with a windmill sprayer. Spray treatments were applied on Jun. 20, Jun. 26, Jul. 3, Jul. 10, Jul. 26, Aug. 6, and Aug. 15. The following table sets forth the results of the field trial (application dates are in bold face):

| Field Trial Using Beta to Control Two Spotted Spider Mites | | | | | |
| --- | --- | --- | --- | --- | --- |
| Lower Leaves | | | Upper Leaves | | |
| 15 gallon | 100 gallon | 200 gallon | 15 gallon | 100 gallon | 200 gallon |
| June 20 50% Kill | 100% Kill | 100% Kill | Less than 50% Kill | 85% Kill | 85% Kill |
| June 26 50% Kill | 100% Kill | 100% Kill | Less than 50% Kill | 85% Kill | 85% Kill |
| July 03 50% Kill | 100% Kill | 100% Kill | Less than 50% Kill | 85% Kill | 85% Kill |
| July 10 50% Kill | 100% Kill | 100% Kill | Less than 50% Kill | 85% Kill | 85% Kill |
| July 26 50% Kill | 100% Kill | 100% Kill | Less than 50% Kill | 85% Kill | 85% Kill |
| August 6 50% Kill | 100% Kill | 100% Kill | Less than 50% Kill | 85% Kill | 85% Kill |
| August 15 50% Kill | 100% Kill | 100% Kill | Less than 50% Kill | 85% Kill | 85% Kill |

The 100 and 200 gallon applications were found to kill mites at the rate of 100% on lower hop leaves after every application and 85% on upper leaves. The 15 gallon application had about 50% kill rate on lower leaves and less than that on the upper leaves. It also appeared that powdery mildew was controlled on these plots. Nevertheless, it was discovered that the emulsions tended to clog the sprayers.

C. Follow-Up Tests.

In subsequent field tests, it was discovered that solubility and film problems associated with beta acids could be improved considerably by adding liquid soap at 0.5% concentration.

It has been further discovered that beta acids may be effective in controlling the late blight organism on potato leaves and may have potential for use as a fungicide on organically-grown potatoes and tomatoes. It is possible that beta acids can be applied on tomatoes to control black mold disease. At the 1% concentration, beta acids have shown good suppression of spore formation in hop powdery mildew colonies that were already formed. This is an important development because it can be used to treat powdery mildew infections that are already in existence in a hop field. Powdery mildew is also a problem with wine grapes.

The invention described above is not to be limited by the above examples. It is to be limited only by the following claims, which are to be interpreted according to established doctrines of claim interpretation. The terms “hop acids,” “solution,” and “emulsion” are to be interpreted as used above and as they are understood in the hop industry.

What is claimed:

1. A method for controlling spider mites in an agricultural crop, the method comprising:

applying an aqueous emulsion comprising an emulsifier, soap and at least 1.0% hop beta acids as the sole active agent to the crop, wherein soap is present in an amount sufficient to reduce film in the emulsion.

2. A method for controlling powdery mildew in an agricultural crop, comprising:

applying an emulsion comprising an emulsifier, soap and at least 1.0% hop beta acids to the crop, wherein soap is present in an amount sufficient to reduce film in the emulsion.

3. The method of claim 1 or 2, wherein the emulsion comprises about 0.5% liquid soap.

4. The method of claim 1 or 2, wherein the emulsion comprises about 0.2%, 0.4%, or 2% of an emulsifier.

5. The method of claim 1, wherein the method causes mite mortality.

6. The method of claim 2, wherein the method reduces spore formation.

7. The method of claim 2, wherein the method treats powdery mildew already present on the crop.

8. The method of claim 1 or 2, wherein beta acids are present at about 1% to 10%.

9. The method of claim 1 or 2, wherein the emulsion is stable when stored.

10. The method of claim 1 or 2, wherein the emulsion is stable when diluted.

11. A method for controlling spider mites in an agricultural crop, the method comprising:

applying an aqueous emulsion comprising an emulsifier, soap and at least 1.0% hop beta acids to the crop, wherein soap is present in an amount sufficient to reduce film in the emulsion, wherein the emulsion is free of any other pesticidal active agents.

* * * * *